(12) United States Patent
Nissilä et al.

(10) Patent No.: US 6,575,915 B2
(45) Date of Patent: *Jun. 10, 2003

(54) METHOD AND APPARATUS FOR IDENTIFYING HEARTBEAT

(75) Inventors: Seppo Nissilä, Oulu (FI); Antti Ruha, Oulu (FI); Jari Miettinen, Oulu (FI); Hannu Sorvoja, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

This patent is subject to a terminal disclaimer.

(21) Appl. No.: 09/970,497

(22) Filed: Oct. 4, 2001

(65) Prior Publication Data

US 2002/0120202 A1 Aug. 29, 2002

Related U.S. Application Data

(63) Continuation of application No. 09/202,643, filed as application No. PCT/FI97/00398 on Jun. 19, 1997, now Pat. No. 6,312,387.

(30) Foreign Application Priority Data

Jun. 20, 1996 (FI) .................................................. 962594

(51) Int. Cl.[7] .................................................. A61B 5/00
(52) U.S. Cl. ...................................................... 600/500
(58) Field of Search ............................ 600/485, 453–6, 600/500–3

(56) References Cited

U.S. PATENT DOCUMENTS

| | | |
|---|---|---|
| 4,307,728 A | 12/1981 | Walton |
| 4,802,488 A | 2/1989 | Eckerle |
| 4,893,631 A | 1/1990 | Wenzel et al. |
| 5,243,992 A | 9/1993 | Eckerle et al. |
| 5,269,312 A | 12/1993 | Kawamura et al. |
| 5,273,046 A | 12/1993 | Butterfield et al. |
| 5,467,771 A | 11/1995 | Narimatsu et al. |
| 5,494,043 A | 2/1996 | O'Sullivan |
| 5,497,779 A | 3/1996 | Takaya et al. |

FOREIGN PATENT DOCUMENTS

| | | |
|---|---|---|
| EP | 0 404594 A2 | 12/1990 |
| SE | 8003106-5 | 9/1982 |

*Primary Examiner*—Robert L. Nasser
(74) *Attorney, Agent, or Firm*—Hoffman & Baron, LLP

(57) ABSTRACT

The invention relates to a method and an apparatus for identifying a heartbeat. In the method, an arterial pressure signal is measured in the form of multichannel measurement, and the required signal-processing operations, such as filtration, are carried out if necessary. The method also comprises carrying out signal detection and decision-making concerning the acceptance as a heartbeat signal. According to the invention, the signal detection includes multichannel channel-specific detection for the purpose of identifying signal components of different channels, and the obtained channel-specific detected channel signals are used as input data during the decision-making stage.

32 Claims, 4 Drawing Sheets

METHOD AND APPARATUS FOR IDENTIFYING HEARTBEAT

This application is a continuation of 09/202,643, filed Aug. 30, 1999, now U.S. Pat. No. 6,312,387, which is a 371 of PCT/FI97/00398, filed Jun. 19, 1997.

BACKGROUND OF THE INVENTION

1. Field of the Invention

The invention relates to a method for identifying a heartbeat, the method comprising measuring an arterial pressure signal in the form of a multichannel measurement, and carrying out signal-processing operations, such as filtration, if necessary, and performing signal detection and decision-making concerning the identification of a signal as a heartbeat signal.

The invention also relates to an apparatus for identifying a heartbeat, the apparatus comprising a multichannel sensor, preferably a signal-processing means for processing a signal obtained from the multichannel sensor, detection means for detecting a signal, and decision-making means for identifying the signal as a heartbeat signal.

2. Brief Description of the Prior Art

Prior art conventional arrangements for heartbeat measurement performed on an arterial pressure pulse are based on the use of one sensing element, in other words the measurement is carried out via one channel. The problem is, however, that heartbeat measurement, based on the use of one sensing element, from an arterial pressure pulse is only accurate when the subject is at rest and interference is minimal. The movement of a limb, a tendon or a muscle creates significant interference in the signal measured by the sensor, which may result in an unsuccessful measurement. The problem is aggravated by the similarity in frequency bands and waveforms of the interference and the actual signal in an individual measurement channel, which makes it more difficult to distinguish the signal from interference.

Arrangements utilizing multichannel measurement are also known. Multichannel measurement of a pressure pulse provides better capacity than a one-channel method. In a multichannel pressure pulse signal, the interference is mainly common-mode or similar amongst different channels, which enables elimination of interference caused by movement of the subject. A known method is disclosed in U.S. Pat. No. 5,243,992. The method disclosed in this reference utilizes a multichannel tonometer sensor. The signal processing utilizes known methods for decreasing interference signals, such as band-pass filtration and subtraction of an average of signals of all channels from each channel signal. In U.S. Pat. No. 5,243,992, the heartbeat detection is based on the selection of the best signal channel. The pulse in the selected channel is accepted as a heartbeat pulse by means of a correlation function. A few preceding pulse amplitudes are used as the selection criteria for the channel. Such selection of one channel leads to uncertain operation during interference situations and when the sensor moves with respect to the artery. Due to the high interference level, the method based on the selection of one channel may lead to the selection of a channel other than the one with the best heartbeat signal. Also, when the heartbeat of a moving person is measured, the movement of the sensor at the wrist with respect to the artery may transfer the heartbeat signal to a different channel, and therefore the signal may be lost for a while until a channel providing a good signal is located again. Also, the use of mathematical operations, such as a correlation function, requires a great deal of calculation capacity, in which case implementation of a signal processor is required, which in turn leads to a large size and great consumption of energy. Other known multichannel measurement methods are disclosed in EP 404,594 and SE 425,290.

SUMMARY OF THE INVENTION

The purpose of the present invention is to provide a new type of method and system avoiding the problems of the prior arrangements.

In order to achieve this, the method according to the invention is characterized in that in the method the signal detection includes multichannel channel-specific detection for the purpose of identifying signal components of different channels. The channel-specific detected channel signals obtained are used as input data in the decision-making stage.

In order to achieve this, the apparatus according to the invention is characterized in that the detection means are arranged to carry out multichannel channel-specific detection on several different channels. The decision-making means are connected to perform identification of a heartbeat signal from among several channel signals detected specifically for each channel.

The invention provides several advantages. The arrangement according to the invention provides better reliability and capacity with the use of more than one signal channel for the detection of a heartbeat or pulse. Movement of the sensor with respect to the artery does not necessarily remove the signal from all the channels, as might happen in a one-channel method. The algorithm according to the method of the invention can be implemented in a simple manner with, for example, a general-purpose processor or a digital or preferably analog ASIC, which provides a wrist-watch-like small and light apparatus operated with a battery. The preferred embodiments of the invention and other more detailed embodiments accentuate the advantages of the invention.

The invention will be described in greater detail below by means of examples with reference to the accompanying drawings, in which

DETAILDE DESCRIPTION OF THE INVENTION

Figure 1:
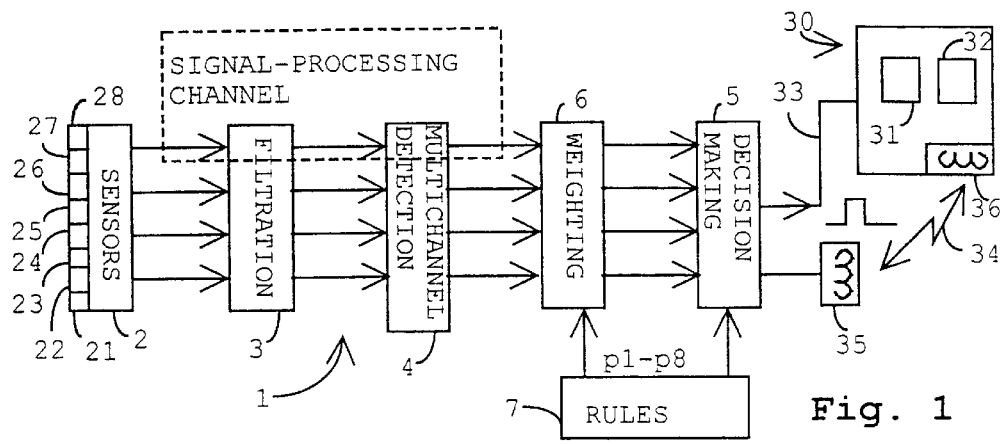
FIG. 1 shows an apparatus according to the invention.
Figure 2:
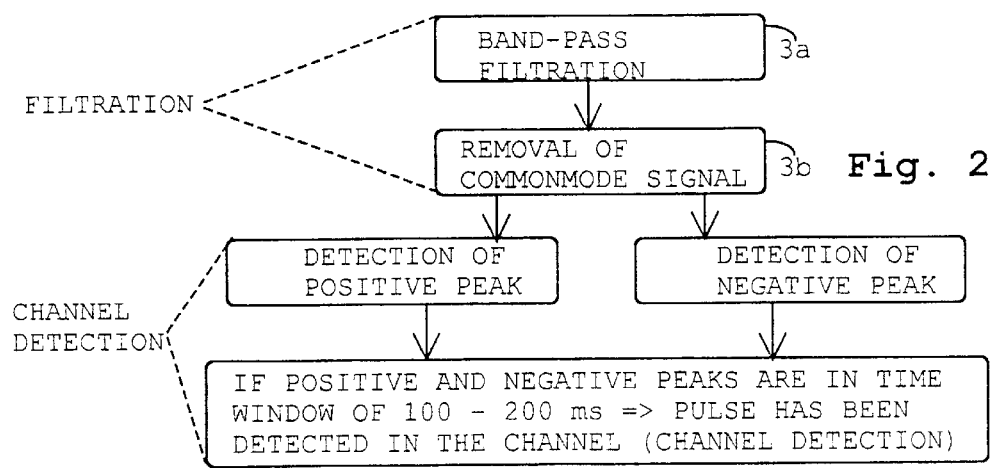
FIG. 2 shows one signal-processing channel of FIG. 1.

A block diagram of the apparatus/method according to the invention is shown in FIG. 1. The invention relates to an apparatus for identifying a heartbeat. The apparatus comprises a multichannel sensor 2 and preferably signal-processing means 3, which most preferably includes filtration means 3, for processing a signal obtained from the multichannel sensor 2. In FIG. 2, the filtration means 3 is divided into two blocks 3a and 3b.

The apparatus for identifying a heartbeat also comprises detection means 4 for carrying out signal detection, and decision-making means 5 for identifying a signal as a heartbeat signal.

Figure 3:
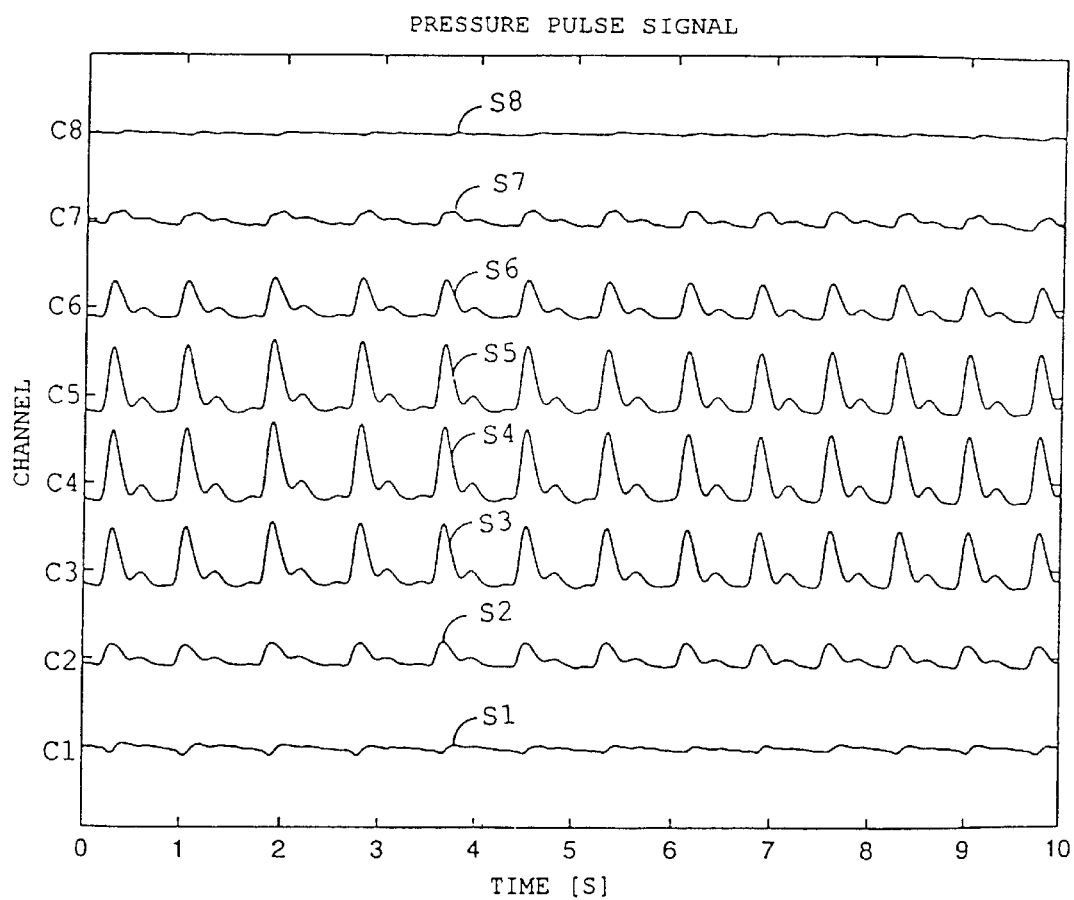
FIG. 3 shows a multichannel pressure pulse signal.
Figure 4:
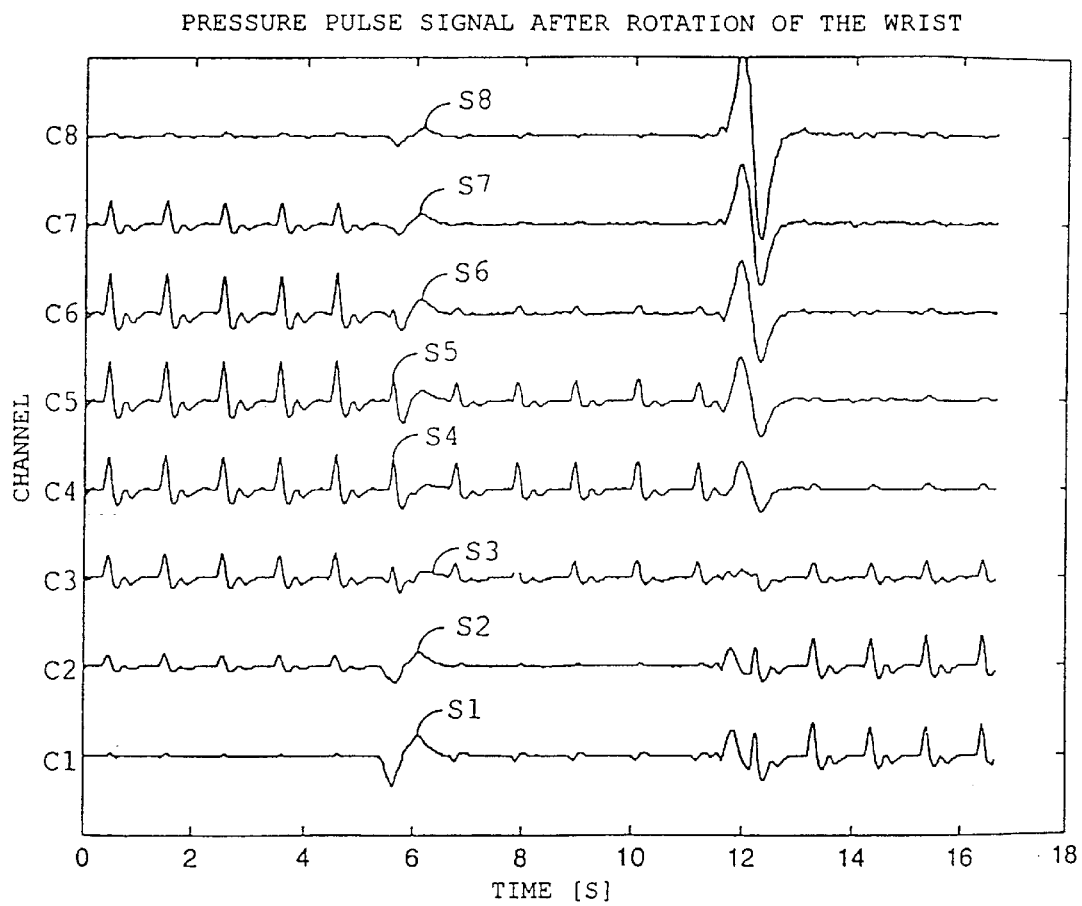
FIG. 4 shows a multichannel pressure pulse signal after the wrist has been rotated.
Figure 6:
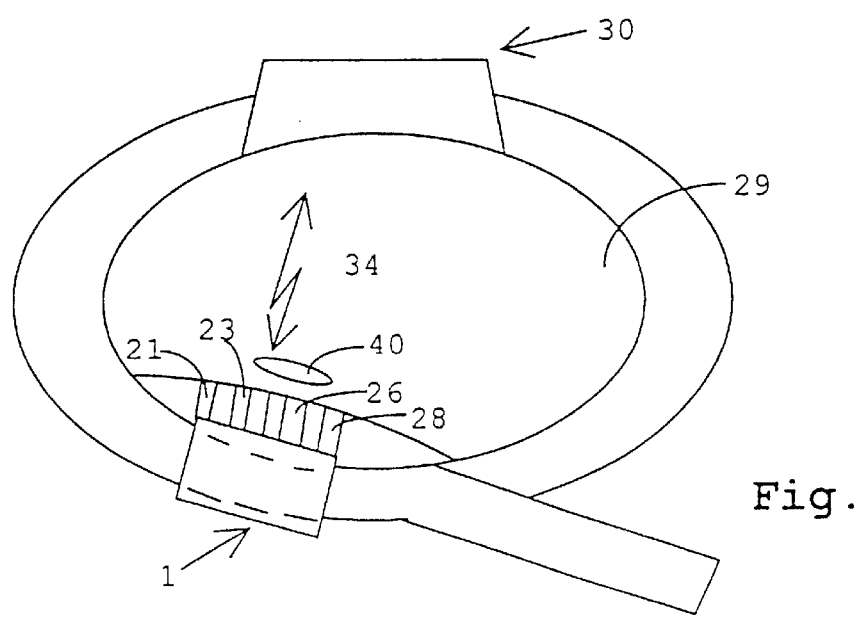
FIG. 6 shows a pulse rate meter wrist strap placed on the wrist and comprising an apparatus according to the invention integrated therein.

FIGS. 1 and 6 show that the multichannel sensor 2 comprises, for example, eight sensing elements 21 to 28. Correspondingly, FIGS. 3 and 4 illustrating pressure pulse signals S1 to S8 show channels C1 to C8 corresponding to the sensing elements 21 to 28. The multichannel sensor 2 may be any sensor, for example a PVDF sensor based on the piezoelectric effect or, for example, an electromechanical film (EMF) sensor based on an electret film. FIG. 6 shows a pulse rate meter wrist strap 30 wrapped around a person's wrist 29 with an associated apparatus 1 according to the invention for identifying a heartbeat. The block 30 that represents a pulse rate meter or some other so-called host apparatus is also shown in FIG. 1. The pulse rate meter 30 or some other host apparatus includes calculation means 31, a display 32 and possibly also other components typically found in wrist-worn pulse rate meters, such as a Telemetric heartbeat receiver, a keypad for inputting data, and connection means for transferring data to a personal computer. The connection between the apparatus 1 and the apparatus 30 may be wired or wireless. If the connection is wired, the apparatus 1 and the apparatus 30 are most preferably integrated into the same apparatus. Reference numeral 33 denotes a wired connection.

In the situation shown in FIG. 6, the connection is wireless, i.e. between the apparatus 1 and the apparatus 30 there is a telemetric remote readable connection 34 via remote readable means 35 and 36, such as remote readable coils 35 and 36. The remote reading technique which is based on magnetic inductive coupling, is based on oscillating circuits producing magnetic oscillation.

The apparatus 1 is characterized in that the detection means 4 are arranged to carry out multichannel channel-specific detection for several different channels C1 to C8 and that the decision-making means 5 are connected to identify a heartbeat signal from among the numerous channel signals specifically detected from each channel. In the method, a pressure signal in an artery 40 is measured in the form of a multichannel measurement, and preferably the signal-processing, such as filtration, is carried out, as well as signal detection and decision-making concerning the identification of a signal as the heartbeat signal. Signal detection in the present invention includes multichannel channel-specific detection for the purpose of identifying signal components of different channels. The channel-specific detected channel signals obtained are used as input data in the decision-making stage in the block 5. In the preferred embodiment of the invention, the multichannel channel-specific detection includes identification of the heartbeat pulse component of the pressure signal as part of the identification of the signal components of the different channels.

FIG. 6 shows that the multichannel sensor 2 is positioned such that at least one sensing element of the sensor 2, for example elements 23 to 26, is placed over the artery 40, and that at least one other sensing element of the sensor 2, for example elements 21 to 22 and 27 to 28, is not situated over the artery 40. Thus, in addition to a measurement carried out from a point with a heartbeat signal, such as by elements 23 to 26, the method also comprises measurement from a point with no heartbeat signal, such as by elements 21 to 22 and 27 to 28. Correspondingly, in addition to the formation of at least one channel signal having a heartbeat pulse in the channel-specific detection, at least one channel signal with no heartbeat pulse is also formed. The measurement of a channel containing no heartbeat, e.g. channel C8, is utilized in the signal filtration, since by means of the signal S8 of the channel C8 having no heartbeat it is possible to determine the average value of the common-mode interference signal.

As shown in FIG. 6, signals obtained from the multichannel pressure sensor are thus filtered both specifically for each channel, such as by individual band-pass filtration in block 3a, and with respect to the other channels, such as by canceling the common-mode interference signal in block 3b. Stated differently, the procedure is such that the signal of each channel C1 to C8 is strengthened and the interference is reduced by subjecting the signal S1 to S8 of each channel C1 to C8 to individual band-pass filtration in step 3a, and by subtracting the value that represents the common-mode interference signal of the signals on adjacent channels in step 3b. The order in which these steps 3a, 3b are carried out may be different from that disclosed above.

Figure 5:
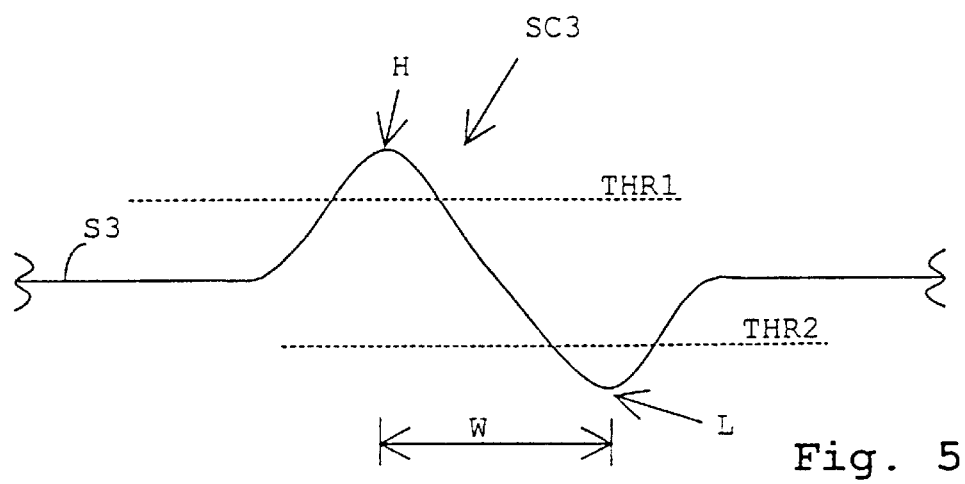
FIG. 5 shows a heartbeat pulse component of a pressure signal, and detection thresholds used for detecting it.

In a preferred embodiment of the invention, a pressure pulse is detected from the signal of each channel by detecting positive peaks H and negative peaks L of the filtered signal within a time window W, which is preferably predetermined. In the preferred embodiment, the detection of the channel signal utilizes a fixed or changing time window W. Detection of a peak value is simple and advantageous. In order to simplify the arrangement, it is noted with reference to FIGS. 2 and 5 that the detection utilizes detection thresholds THR1 and THR2, and that these detection thresholds are either fixed and common to all channels, adaptive and common to all channels or adaptive specifically for each channel. FIG. 5 may represent for example signal S3 as regards its heartbeat pulse component SC3. Detection threshold THR1 shows the detection threshold of the positive peak value H, and detection threshold THR2 shows the detection threshold of the negative peak value L. With reference to FIG. 2, it is stated that this time delay between the peak and the minimum, i.e. the time window W, is most preferably about 100 to 200 milliseconds.

To further improve the efficiency and adaptivity of the invention, in the preferred embodiment, the apparatus 1 comprises weighting means 6 for weighting the contribution of one or several channels differently from the other channels. The apparatus 1 most preferably comprises a rule block 7 that controls the weighting means 6. The rule block 7 is also connected to and controls the decision-making block 5.

In the preferred embodiment, the channel signals C1 to C8 are weighted for the purpose of decision-making depending on how the heartbeat pulse, e.g. SC3, has occurred previously in the aforementioned channels, e.g. in channel C3. The weighting can be carried out either before the detection or most preferably after the detection, as shown in the figures.

In the preferred embodiment of the invention, the weighting utilizes weighting coefficients p1 to p8 that can be updated, as shown in FIG. 1. The weighting coefficients are then updated on the basis of empirical rules stored in the block 7.

In the preferred embodiment of the invention, an effective empirical rule determines that if a signal having similar characteristics has been detected in adjacent channels in previous measurements, during the decision-making these channels are weighted heavily more than the other channels. FIG. 3 shows that channels C3 to C6 comprise similar signals in adjacent channels, and therefore the weighting coefficients p3 to p6 are updated so that in later measurements, either during the same measurement period or in a separate subsequent measurement, the channels C3 to C6 will be weighted more heavily.

In the preferred embodiment of the invention, if a signal having similar characteristics has been detected in one or more non-adjacent channels in previous measurements, during the decision-making these channels are weighted less heavily than the other channels. In such a case, the weighting coefficients are updated so that in subsequent measurements, either during the same measurement period, or in a separate measurement these non-adjacent channels will be weighted less heavily.

The weighting is therefore most preferably adaptive and emphasizes the favors those channels from which a pressure pulse signal has been previous detected. The decision-making concerning the identification as a heartbeat signal is based on the number of channels C1 to C8 in which the desired signal has occurred on average. The weighting coefficients p1 to p8 are continuously updated on the basis of the empirical rules, so that as the sensors 21 to 28 move with respect to the artery 40, the algorithm is capable of rapidly locating the channels where the desired signal occurs. For instance, when the wrist is turned, the sensors move with respect to the artery and the heartbeat signal moves from one channel to an adjacent channel. Thus, the heartbeat signal does not jump from one channel to another randomly, but moves in a relatively predictable manner as shown in the transition from FIG. 3 to FIG. 4. Specifically, the movement of the sensing elements 21 to 28 of the sensor 2 with respect to the artery 40 and the resulting transfer of the heartbeat signals to different channels is illustrated by a comparison of FIGS. 3 and 4. In FIG. 3, the heartbeat signals can be detected on channels C3 to C6. In FIG. 4, as a result of a rotation of the wrist 29 or some other movement or some other interfering factor, the heartbeat signals have moved to other channels and they now constitute signals S5 to S8 on channels C5 to C8.

In the preferred embodiment of the invention, the decision concerning the identification of a heartbeat signal is carried out in the decision-making stage on the basis of the cross-correlation of signals in two or more adjacent channels. In a preferred embodiment, the decision is carried out in the decision-making stage on the basis of common-mode signals occurring simultaneously in two or more adjacent channels. According to the Applicant, the comparison of two or more adjacent channels is an effective manner to reach a decision. For instance, FIG. 3 shows that adjacent channels C3 to C6 contain common-mode signals S3 to S6 that occur simultaneously and indicate a heartbeat.

When a heartbeat signal cannot be identified on the basis of monitoring two or more adjacent channels, in the next step of the invention, the decision in the decision-making stage is carried out on the basis of a signal that occurs regularly in one channel, such as when only one channel detects a heartbeat and the remaining channels are either non-responsive (i.e., flat-line) or detect pulses that are well below a predetermined noise floor or interference threshold.

The apparatus may be implemented by means of analogue or digital technology, microprocessor technology, or a combination thereof. As regards the components, they may consist of discrete components, integrated circuits or a combination thereof.

Even though the invention is described above with reference to examples according to the accompanying drawings, it is clear that the invention is not restricted thereto, but it can be modified in several ways within the scope of the inventive idea disclosed in the appended claims.

What is claimed is:

1. A method for identifying a heartbeat comprising the steps of:
   measuring an arterial pressure signal in the form of multi-channel measurement; and
   performing signal detection and decision-making concerning the identification of a heartbeat signal;
   wherein said signal detection includes multi-channel channel-specific detection for the purpose of identifying signal components of different channels, and said obtained channel-specific detected channel signals are used as input data in said decision-making, whereby said heartbeat signal includes data from at least two channels.

2. A method according to claim 1, further including the step of weighting said channel signals for said decision-making based on the heartbeat signal previously occurring in said channels.

3. A method according to claim 2, further including the step of weighting utilizing weighting coefficients that can be updated.

4. A method according to claim 3, further including the step of updating said weighting coefficients on the basis of empirical rules.

5. A method according to claim 4, further including the step of weighting adjacent channels having similar signals more than other channels during said decision-making.

6. A method according to claim 4, further including the step of weighting non-adjacent channels having similar signals less than other channels during said decision making.

7. A method according to claim 2, further including the step of weighting after said channel-specific detection and before said decision-making.

8. A method according to claim 1 further including the step of performing signal detection and decision-making concerning the identification of a signal as a non-heartbeat signal.

9. A method according to claim 1 further including the step of forming at least one channel signal with no heartbeat signal.

10. A method according to claim 1 further including the step of filtering said signals both specifically for each channel and with respect to the other channels.

11. A method according to claim 1 further including the step of reducing the interference of each channel by subjecting the signals of all of said channels to band-pass filtration and subtracting a common-mode interference signal from said signal of each channel.

12. A method according to claim 1, further including the step of obtaining said signals from the artery at the wrist by using a wrist strap including a sensor.

13. An apparatus for identifying a heartbeat comprising:
   a multichannel sensor, the multichannel sensor measuring an arterial pressure signal in the form of a multichannel measurement;
   detection means, the detection means detecting a signal; and
   decision-making means, the decision making means performing decision-making concerning the identification of the signal as a heartbeat signal, said detection means performing multichannel channel-specific detection for the purpose of identifying signal components of different channels, channel-specific detected channel signals being used as input data to said decision-making means, a decision being made by said decision-making means on the basis of cross-correlation of signals occurring in two or more adjacent channels.

14. An apparatus according to claim 13 further comprising weighting means, the weighting means weighting said signals of one or more channels differently from the other channels.

15. An apparatus according to claim 14 further comprising a rule means, the rule means controlling said weighting means.

16. An apparatus according to claim 13 wherein said multichannel sensor is positioned such that at least one sensing element is situated over the artery and at least one other sensing element is not situated over the artery.

17. An apparatus according to claim 13 further including signal processing means, the signal processing means processing a signal obtained from said multichannel sensor, said signal processing means being coupled to said detection means.

18. An apparatus for identifying a heartbeat comprising:
   a multichannel sensor, the multichannel sensor measuring an arterial pressure signal in the form of a multichannel measurement;
   detection means, the detection means detecting a signal; and
   decision-making means, the decision making means performing decision-making concerning the identification of the signal as a heartbeat signal, said detection means performing multichannel channel-specific detection for the purpose of identifying signal components of different channels, channel-specific detected channel signals being used as input data to said decision-making means, a decision being made by said decision-making means on the basis of common-mode signals occurring simultaneously in two or more adjacent channels.

19. An apparatus according to claim 18 further comprising weighting means, the weighting means weighting said signals of one or more channels differently from the other channels.

20. An apparatus according to claim 19 further comprising a rule means, the rule means controlling said weighting means.

21. An apparatus according to claim 18 wherein said multichannel sensor is positioned such that at least one sensing element is situated over the artery and at least one other sensing element is not situated over the artery.

22. An apparatus according to claim 18 further including signal processing means, the signal processing means processing a signal obtained from said multichannel sensor, said signal processing means being coupled to said detection means.

23. An apparatus for identifying a heartbeat comprising:
   a multichannel sensor, the multichannel sensor measuring an arterial pressure signal in the form of a multichannel measurement;
   detection means, the detection means detecting a signal; and
   decision-making means, the decision making means performing decision-making concerning the identification of the signal as a heartbeat signal, said detection means performing multichannel channel-specific detection for the purpose of identifying signal components of different channels, channel-specific detected channel signals being used as input data to said decision-making means, a decision being made by said decision-making means on the basis of a signal occurring regularly in one channel when said heartbeat signal cannot be identified on the basis of monitoring two or more adjacent channels.

24. An apparatus according to claim 23 further comprising weighting means, the weighting means weighting said signals of one or more channels differently from the other channels.

25. An apparatus according to claim 24 further comprising a rule means, the rule means controlling said weighting means.

26. An apparatus according to claim 23 wherein said multichannel sensor is positioned such that at least one sensing element is situated over the artery and at least one other sensing element is not situated over the artery.

27. An apparatus according to claim 23 further including signal processing means, the signal processing means processing a signal obtained from said multichannel sensor, said signal processing means being coupled to said detection means.

28. An apparatus for identifying a heartbeat comprising:
   a multichannel sensor, the multichannel sensor measuring an arterial pressure signal in the form of a multichannel measurement;
   detection means, the detection means detecting a signal; and
   decision-making means, the decision making means performing decision-making concerning the identification of the signal as a heartbeat signal, said detection means performing multichannel channel-specific detection for the purpose of identifying signal components of different channels, said detection means identifying a heartbeat pulse component of said arterial pressure signal as part of said signal components of said different channels, channel-specific detected channel signals being used as input data to said decision-making means.

29. An apparatus according to claim 28 further comprising weighting means, the weighting means weighting said signals of one or more channels differently from the other channels.

30. An apparatus according to claim 27 further comprising a rule means, the rule means controlling said weighting means.

31. An apparatus according to claim 28 wherein said multichannel sensor is positioned such that at least one sensing element is situated over the artery and at least one other sensing element is not situated over the artery.

32. An apparatus according to claim 28 further including signal processing means, the signal processing means processing a signal obtained from said multichannel sensor, said signal processing means being coupled to said detection means.

* * * * *

UNITED STATES PATENT AND TRADEMARK OFFICE
CERTIFICATE OF CORRECTION

PATENT NO.   : 6,575,915 B2
DATED        : June 10, 2003
INVENTOR(S)  : Nissilä et al.

It is certified that error appears in the above-identified patent and that said Letters Patent is hereby corrected as shown below:

<u>Title page,</u>
Item [74], now reads "Hoffman & Baron, LLP" should read -- Hoffmann & Baron, LLP --;

<u>Column 2,</u>
Line 56, now reads "DETAILDE DESCRIPTION" should read -- DETAILED DESCRIPTION --.

Signed and Sealed this

Twenty-third Day of September, 2003

JAMES E. ROGAN
*Director of the United States Patent and Trademark Office*